United States Patent [19]

Staehlin et al.

[11] Patent Number: 5,626,581
[45] Date of Patent: May 6, 1997

[54] IMPLANTABLE BONE LENGTHENING APPARATUS

[75] Inventors: John H. Staehlin, Lutherville; Amy Corvelli, Baltimore, both of Md.; Stanley Lu, Bridgewater, N.J.; Garret Taylor, Olean, N.Y.

[73] Assignee: Volunteers for Medical Engineering, Baltimore, Md.

[21] Appl. No.: 562,872

[22] Filed: Nov. 27, 1995

[51] Int. Cl.$^6$ .................................................. A61B 17/56
[52] U.S. Cl. .......................... 606/63; 606/62; 606/67; 606/68; 606/78; 606/53
[58] Field of Search .................. 606/60, 62, 63, 606/64, 67, 68, 76, 78, 53

[56] References Cited

U.S. PATENT DOCUMENTS

| | | | |
|---|---|---|---|
| 4,945,727 | 8/1990 | Whitehead et al. | 60/527 |
| 5,356,411 | 10/1994 | Spievack | 606/63 |
| 5,415,660 | 5/1995 | Campbell et al. | 606/67 |
| 5,466,261 | 11/1995 | Richelsoph | 606/63 |

*Primary Examiner*—Michael Powell Buiz
*Assistant Examiner*—Mark S. Leonardo
*Attorney, Agent, or Firm*—Finnegan, Henderson, Farabow, Garrett & Dunner

[57] ABSTRACT

An implantable bone lengthening apparatus may utilize an entirely self-contained lengthening mechanism which includes a shape memory material-powered hydraulic pump, a shape memory material-powered ratchet mechanism, a permeable head piston mechanism, and a bellows extension mechanism. The bone lengthening nails are more compact, simpler, eliminate unnecessary shifting or torsional movement, and maintain alignment of the bone during its natural healing process.

24 Claims, 8 Drawing Sheets

FIG. 10

IMPLANTABLE BONE LENGTHENING APPARATUS

BACKGROUND OF THE INVENTION

1. Field of the Invention

This invention relates to the field of orthopedic surgery, and to the field of implantable bone lengthening devices.

2. Description of the Related Art

The typical apparatus used for bone lengthening consists of a special nail implanted in a cavity formed by the removal of the bone marrow from, for example, a leg bone. With the nail in place, an external longitudinally-adjustable frame assembly is secured to the ends of the bone. One end of the frame is pinned to an end of the bone and the other end of the frame is pinned to the other end of the bone having the nail located therein. The bone is then broken and this adjustable frame is periodically lengthened causing the bone, as the break is knitting, to also lengthen. This external frame fixation system is difficult to securely locate on the patient, resulting in discomfort and an unattractive appearance. More seriously, the pins, being secured in the bone and protruding outside of the skin, increase the risk of infection.

Thus, there is a need for a bone lengthening device which incorporates an extension mechanism into the structure of the implantable nail body, thereby eliminating the need for this external frame and all of its related problems.

SUMMARY OF THE INVENTION

It is an object of this invention to provide an implantable lengthening apparatus which forces the ends of a broken bone away from each other while maintaining the bone in alignment.

It is a further object of this invention to provide a means for activating the mechanism totally within the structure of the apparatus requiring no external force for accomplishing the bone lengthening.

It is still a further object of the invention to provide an implantable bone lengthening apparatus which will automatically and periodically adjust the length of the apparatus.

Further objects and advantages of the invention will become apparent from a consideration of the drawings and ensuing description.

It is to be understood that both the foregoing general description and the following detailed description are exemplary and explanatory, and are not restrictive of the invention as claimed.

Additional features and advantages of the invention will be set forth in the description which follows, and in part will be apparent from the description, or may be learned by practice of the invention. The objectives and other advantages of the invention will be realized and attained by the system particularly pointed out in the written description and claims hereof, as well as the appended drawings.

To achieve these and other advantages, and in accordance with the purpose of the invention as embodied and broadly described in the application, the invention discloses a bone lengthening nail assembly comprising a first nail body section and a second nail body section, and a power cartridge comprising a powered hydraulic pump which forces hydraulic fluid from a hydraulic fluid reservoir and into a sealed chamber between the first and second sections thereby forcing the first nail section to extend longitudinally relative to the second nail section, thereby increasing the length of the bone lengthening nail.

In another aspect, the invention includes a hydraulic pump comprising a pump piston body having a first spring comprised of a shape memory material located on one side of the pump piston body, and a second spring located on the opposing side of the pump piston body, wherein the shape memory material has a first phase in which the first spring has a lower elastic modulus than the second spring, and a second phase in which the first spring has a higher elastic modulus than the second spring.

In a further aspect, the invention includes a bone lengthening nail assembly comprising a first nail body section having grooves located therein and a longitudinal axis, a second nail body section, a reciprocating ratchet mechanism located in the second nail body section and extending into the first nail body section, fingers located on the ratchet mechanism which extend into the grooves, and a shape memory material spring assembly attached to the ratchet mechanism which has a first phase in which the spring is compact and a second phase in which the spring is extended.

In another aspect, the invention includes a bone lengthening nail assembly comprising a first nail body section and a second nail body section, a chamber located in the second nail body section, the chamber being filled with fluid, a permeable piston head rigidly attached to the first nail body section and extending into the chamber, and springs which force the permeable piston head to move longitudinally through the chamber, thereby forcing the fluid to permeate through the piston head.

Another aspect of the invention includes a bone lengthening nail assembly comprising a first nail body section and a second nail body section, a chamber located in the second nail body section, a piston head rigidly attached to the first nail body section and extending into the chamber, a longitudinally expanding bellows located in the chamber and rigidly attached to the piston head and second nail body section, and chamber filling means for filling the bellows with a fluid, thereby causing the bellows to expand, and causing the nail to extend.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings:

FIG. 5a illustrates an embodiment of the invention utilizing a shape memory material-powered ratchet assembly;

FIG. 5b is an exploded view of the spring assembly of FIG. 5a;

DETAILED DESCRIPTION OF THE PREFERRED EMBODIMENTS

In a first embodiment, the present invention relates to a hydraulic implantable bone lengthening apparatus designed to be an automatically-operated mechanism in which maximum lengthening of the apparatus is controlled by the amount of fluid present in the reservoir at the start of the process. Referring initially to FIGS. 1–4, a first nail section 1 is inserted into a second nail section outer body 2 by inserting a piston head 3 toward the top end of the second nail section body 2 and pushing it through a seal ring 4 located at the lower end of a second nail section body 2. The first nail section 1 is inserted so that the piston head 3 and its seal ring 5 longitudinally slide in the outer body 2 to increase the length of the apparatus. The power cartridge 6 is locked into the cylinder bore of the second nail section above the piston head 3 with an external seal ring 7 sealing it against the outer body 2, thereby forming a sealed chamber 8 above the piston head 3. The power cartridge 6 has a communicative passage 9 through which incompressible fluid 10 is forced to travel from the reservoir 11 into the sealed chamber 8. The incompressible fluid 10 is propelled by the action of a pump piston body 12 as it is caused to reciprocate under the influence of an opposing spring drive mechanism. The pump piston body 12 has a polished piston section 13 whose longitudinal axis coincides with the longitudinal axis of the first nail section. The polished piston section 13 of the pump piston body 12 operates through a suitable pump piston seal ring 14 as it moves along the longitudinal axis during the pumping action.

The spring drive mechanism uses at least one spring made of a shape memory material. A shape memory material is a material which has the ability to "remember," or return to, a previous shape upon heating by a diffusionless transformation from a first phase to a second phase. A typical example of a shape memory material is nitinol, a compound of nickel and titanium with a nickel content of between about 53% to 57%. In nitinol, the first phase is austenitic. When heated, the nitinol transforms to a martensitic state.

Figure 1:
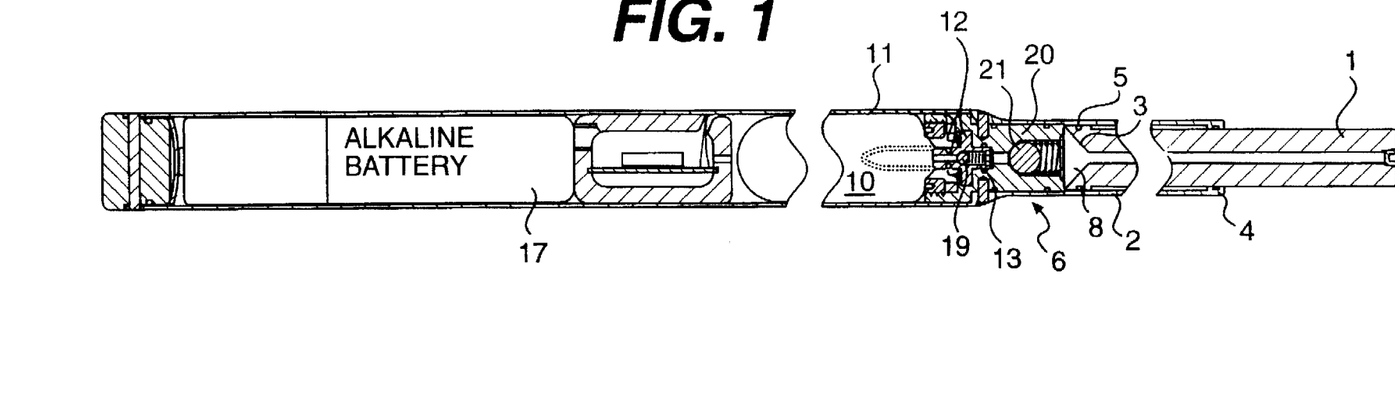
FIG. 1 is a cut-away view of a shape memory material-powered hydraulic pump nail assembly.
Figure 2:
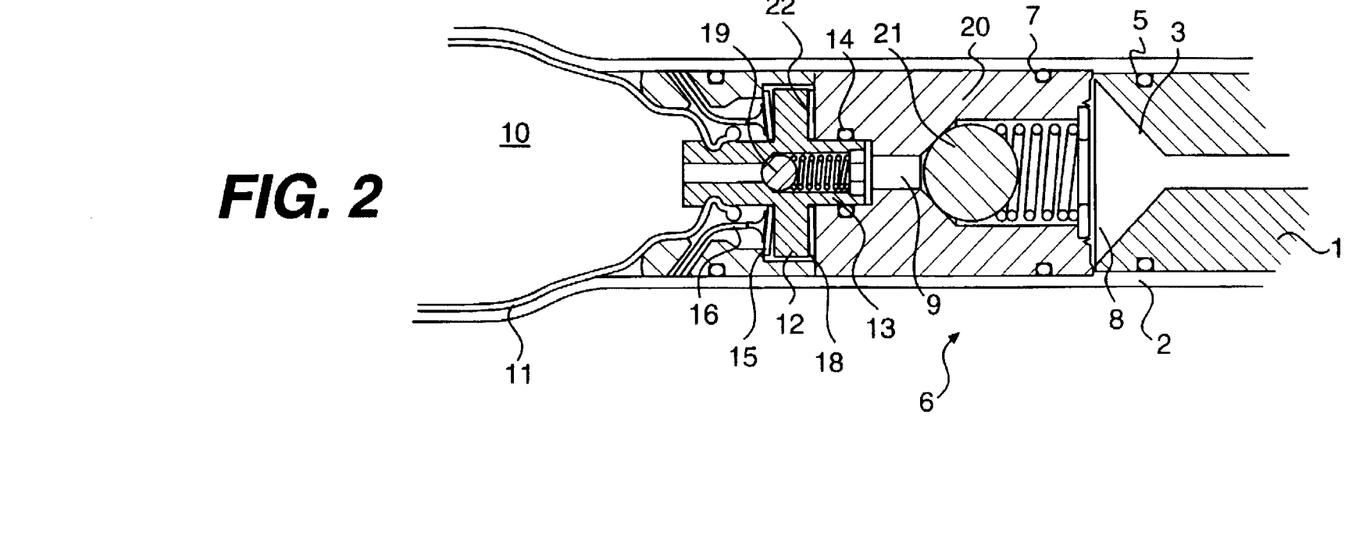
FIG. 2 is a cross-section of the shape memory material-powered hydraulic pump assembly.

The shape memory material power spring 15 is preferably made of nitinol, and is transformed to its martensitic state by raising the temperature of the shape memory material power spring 15 above the trigger temperature by the application of heat which is accomplished through a heater element 16 integral with the surface of the shape memory material power spring 15. The heater element 16 may have integral positive and negative leads through which DC power is applied.

These leads attach to a timer or remote control circuitry package and then to a battery pack 17. The timing circuitry energized by the battery pack 17 periodically sends a current through the resistance heater element 16 integral with the surface of the shape memory material power spring 15.

Figure 3:
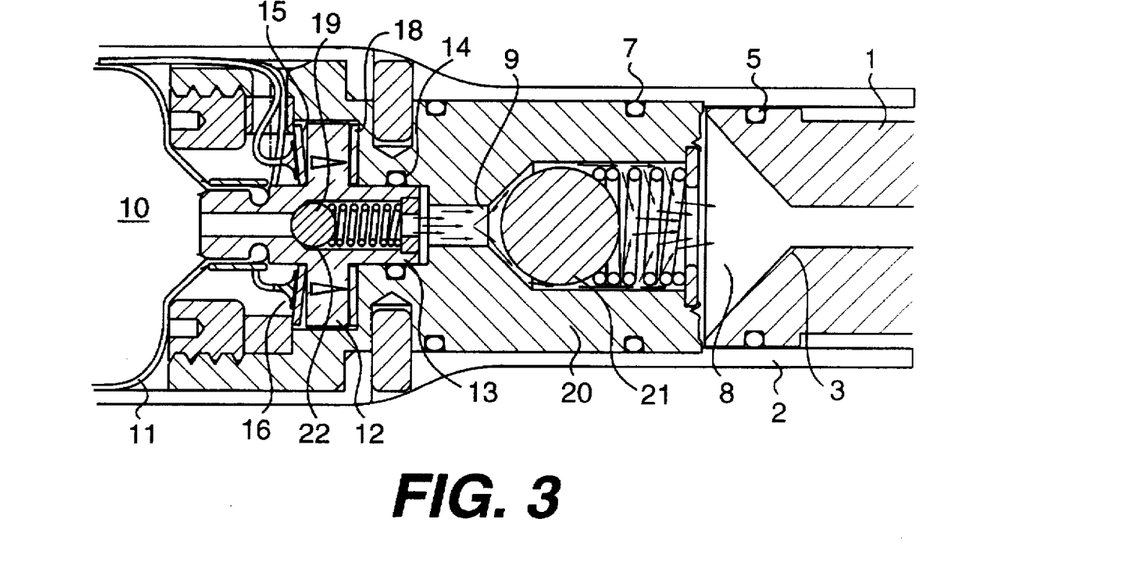
FIG. 3 illustrates the pressurizing stroke of the shape memory material-powered pump.

In FIG. 3, the shape memory material power spring 15 is shown as a belleville spring. A return spring 18 made of a material such as stainless steel, has a higher force than the shape memory material power spring 15 in its austenitic state. When the shape memory material power spring 15 is heated to a certain temperature, the material changes from its austenitic state to its martensitic state. This transformation causes the shape memory material power spring 15 to increase in modulus of elasticity to where its spring force is much greater than that of the stainless steel return spring 18 which then forces the power piston body 12 to translate in the direction of the first nail section 1. This action forces the fluid trapped in front of the polished piston section 13, by the one-way action of a check valve 19, to be injected through the communicative passage 9 into a channel body 20 located downstream from the piston body 12. The channel body 20 has a check valve 21 located therein which enables the fluid to be passed through the channel body 20 and into the sealed chamber 8 where the pressurized incompressible fluid 10 reacts against the piston head 3 and forces the first nail section 1 to longitudinally slide with respect to the second nail section 2. The force driving the piston head 3 is directly proportional to the ratio of the square of the diameter of the piston head 3 compared to the diameter of the polished piston section 13. The force applied by the shape memory material power spring 15 after overcoming the force of the stainless steel return spring 18 is increased by this ratio of cross-sectional areas.

Figure 4:
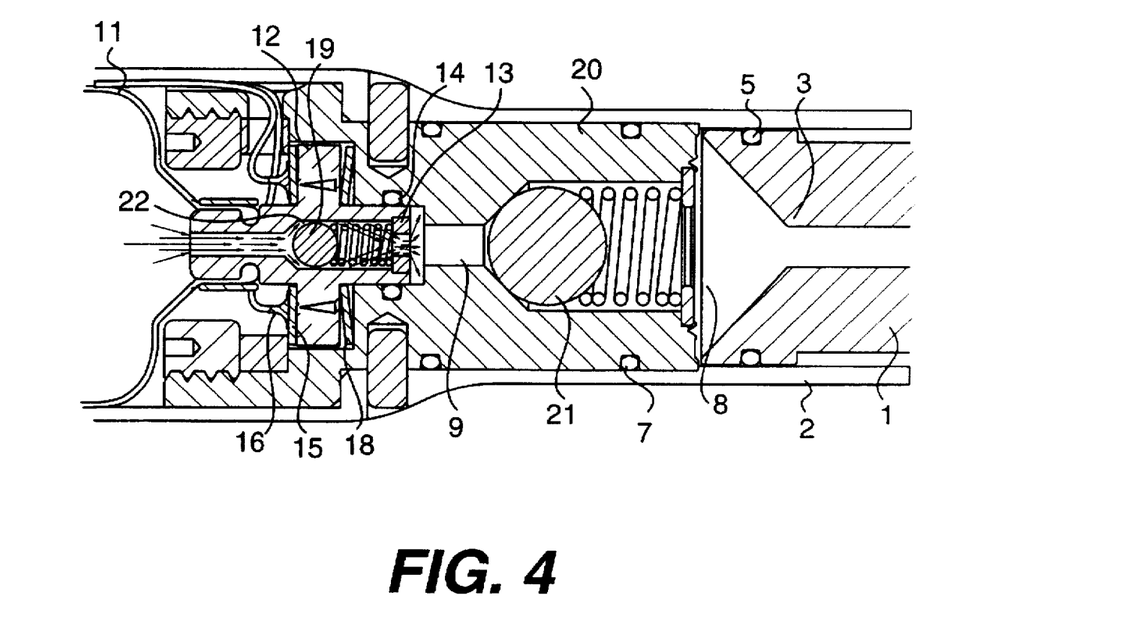
FIG. 4 illustrates the return stroke of the shape memory material-powered pump.

As shown in FIG. 4, when the current is removed from the heating element, the shape memory material power spring 15 reverts back to its austenitic state and its reduced modulus of elasticity. In this state, the stainless steel return spring 18 acting on the sealed chamber 8 side of the pump piston body 12 provides the force to translate the pump piston body 12 away from the sealed chamber 8. The shape memory material power spring 15 acts on the upper surface of the pump piston body 12 working against the action of the stainless steel return spring 18. A communicative passage 22 and the one-way check valve 19 in the pump piston body 12 allow incompressible fluid 10 to move from the reservoir 11 to communicative passage 9. During this return stroke, the check valve 21 in the channel body 20 prevents fluid from passing back through the channel from the sealed chamber 8.

The operation of the hydraulic shape memory material pump-powered apparatus utilizes a continuous supply of liquid feeding the shape memory material-powered piston applying breakaway force pressures at the integral ball check valve. The liquid is contained within the entire chamber between the piston head of the first nail section through the channel body's check valve 21 and the interconnecting passages up to the shape memory material-powered piston's integral ball check valve 19 and ultimately into the elastic expanded balloon reservoir 11.

The following is an explanation of a procedure for initially filling the chamber. Each of the ball check valves must be held open for a period of time during the filling. One method of doing this is to trap a thread of material between the ball and the seat in each check valve so that the free end of the thread facing the piston head of the first nail section is accessible. A pressurization fitting is attached to the housing containing a channel body's check valve. This pressurization fitting is designed with a collapsed bellows end. The thread holding the ball of the ball check valves off of their seats is attached to the inside surface of this collapsed bellows. The chamber is filled with the bellows remaining collapsed with the filling continuing until the reservoir is filled to the desired volume (a function of the length of extension to be used for this application of the bone lengthening apparatus). Filling then continues with the collapsed bellows now released and allowed to freely expand. This action pulls the thread out from the underneath the shape memory material-powered piston's integral ball check valve ball and then out from underneath the larger ball of the channel body's check valve. The pressure created by the expanded elastic balloon is sufficient to crack the contact of the ball and seat of the integral ball check valve assembly in the shape memory material-powered piston but is insufficient pressure to crack the contact between the larger ball and its seat in the main ball check valve assembly. Thus, the fluid is trapped at this main ball check valve seat. The pump assembly is then installed into the second nail section's bore and locked in place. A bleed line in the first nail section is open during this assembly and fluid placed in the second nail section ahead of the main ball check valve assembly is forced out of the bleed line assuring that the entire chamber between the first nail section piston head and the inside surfaces of the expanded reservoir are filled with fluid.

According to another embodiment, a shape memory material spring-driven ratchet-powered bone lengthening apparatus comprises an assembly of a number of interacting sections. There is a first nail section body 101 whose leading tip 102 is rounded to provide ease of insertion into a cavity cut into the bone marrow of the limb to be lengthened. The inside of the first nail section body 101 on the end opposite the leading tip 102 is bored out so that the inside diameter has a series of annular grooves 103 along its length (see FIG. 5a). The cross-section of the grooves can have many shapes but for this embodiment they are shaped like a buttress thread cross-section with the flat section leg of the buttress shape in the direction of the leading tip.

Figures 5A, 5B:
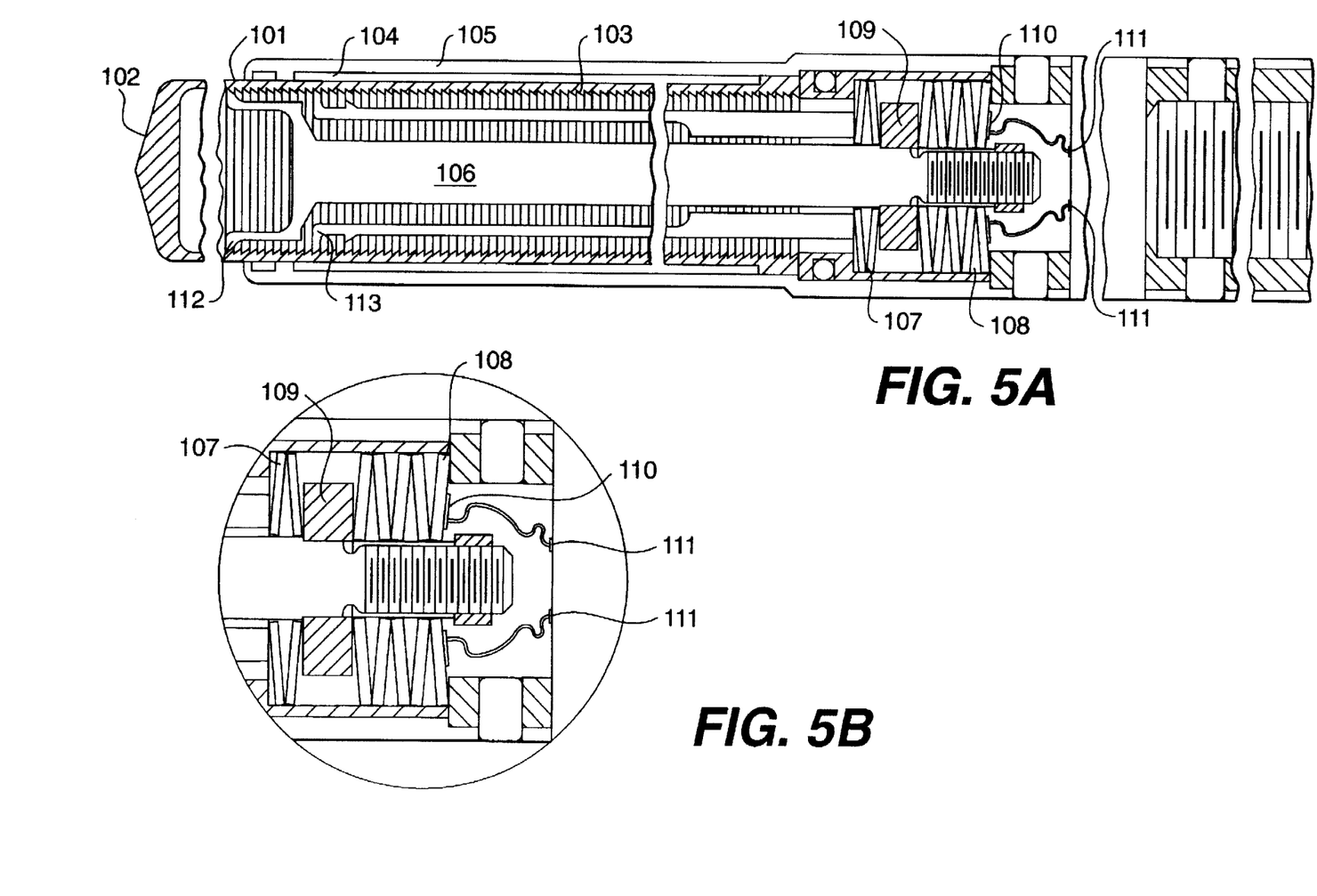
Figure 6A:
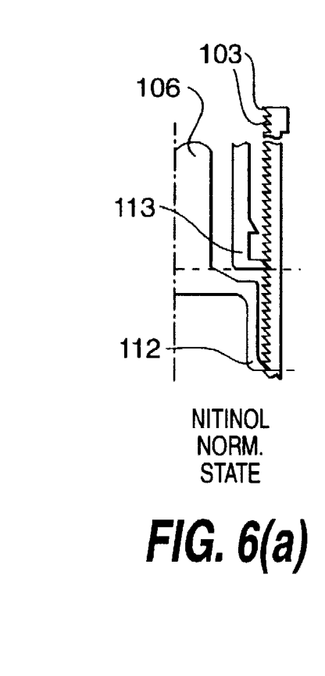
FIG. 6a illustrates the shape memory material ratchet assembly in its resting state.
Figure 6B:
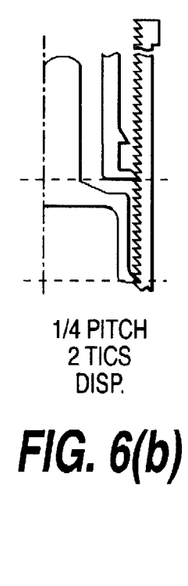
FIG. 6b illustrates the shape memory material ratchet assembly having a displacement of one-quarter pitch.
Figure 6C:
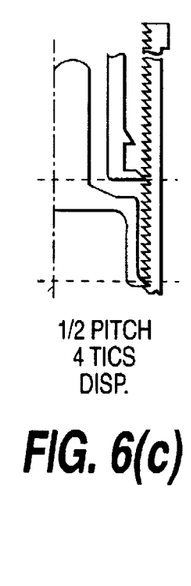
FIG. 6c illustrates a displacement of one-half pitch.
Figure 6D:
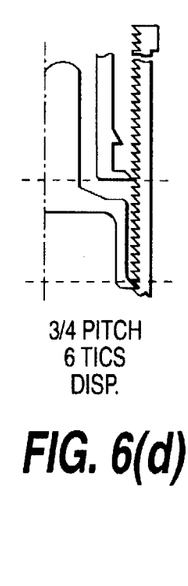
FIG. 6d illustrates a displacement of three-quarter pitch.
Figure 6E:
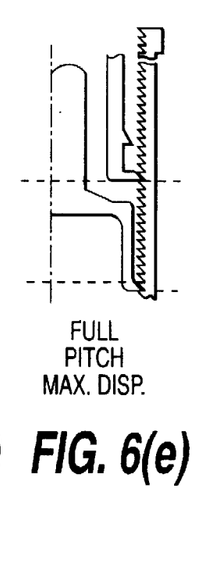
FIG. 6e illustrates a full pitch maximum displacement.
Figure 6F:
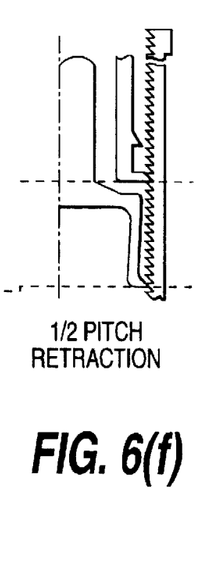
FIG. 6f illustrates the beginning of the retraction step.
Figure 6G:
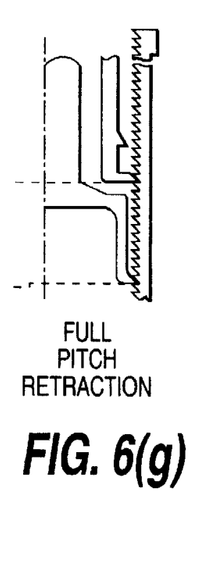
FIG. 6g illustrates a full pitch retraction of the shape memory material-powered ratchet assembly.

The first nail section outer body 101 has an outer diameter that allows its insertion into the first cylinder bore 104 of a second nail section outer body 105. The first nail section outer body 101 slidably translates in the cylinder bore 104 of the second nail section outer body 105 and with a suitable seal ring creates a sealed section above the first nail section 101. Located in this sealed section is the ratchet body 106 whose longitudinal axis is aligned with the longitudinal axis of the first nail section. Stainless steel return spring 107 acts on the ratchet body 106 and provides the force to translate it away from the leading tip 102. The shape memory material power spring 108 acts on the upper surface 109 of the ratchet body 106 working against the action of the stainless steel return spring 107. In its austenitic state, the shape memory material power spring 108 is overpowered by the stainless steel return spring 107 thus allowing the ratchet body 106 to translate away from the leading tip 102.

The shape memory material power spring 108 is transformed to its martensitic state by raising the temperature of the shape memory material power spring 108 above the transition temperature by the application of heat which is accomplished through a heater element 110 integral with the surface of the shape memory material power spring 108. The heater element 110 has integral positive and negative leads 111 through which the DC power is applied to it.

These leads may attach to a timer or remote control circuitry package and then to a battery pack or other power source.

It is recognized that, while the preferred shape memory material for the power spring 108 is nitinol, there are a number of other memory materials which also exhibit the two state phenomena. Additionally, it is recognized that both the stainless steel return spring 107 and the shape memory material power spring 108 can be made in many configurations to accomplish the desired spring action.

The shape memory material-powered ratchet driven implantable bone lengthening apparatus may be designed to be an automatically-operated mechanism whose maximum lengthening is controlled by the number of buttress grooves 103 above the installed position of the ratchet body 106 at the start of the bone lengthening process.

The ratcheting action sequence is shown in FIGS. 6a–6g. The timing circuitry energized by the battery pack periodically sends a current through the resistance heater element 110 integral with the surface of the shape memory material power spring 108. Referring to FIG. 5, the shape memory material power spring 108 is shown as a belleville spring configuration for this embodiment. It is flattened out under the influence of the stainless steel return spring 107 which has a higher force than the shape memory material power spring when it is in its austenitic state. When the shape memory material power spring 108 is heated to a certain temperature, the material changes from its austenitic state to its martensitic state. This transformation causes the shape memory material power spring 108 to increase in modulus of elasticity to where its spring force is much greater than that of the stainless steel return spring 107 which the forces the ratchet body 106 to translate in the direction of the first nail section 101 leading tip 102. This action causes fingers 112 to apply pressure on the flat buttress surface and forces the first nail section 101 to translate with respect to the second nail section 105. The force applied by the shape memory material power spring 108 after overcoming the force of the stainless steel return spring 107 is a function of its size and cross-section which is chosen to provide sufficient force to cause the knitting area of the broken bone to grow.

When the current is removed from the heating element, the shape memory material power spring 108 reverts back to the austenitic state and its reduced modulus of elasticity. In this state, the stainless steel return spring 107 acting on the ratchet body 106 provides the force to translate the ratchet body 106 away from the leading tip 102 of the first nail section 101. The shape memory material power spring 108 acts on the upper surface 109 of the ratchet body 106 working against the action of the stainless steel return spring 107. In its austenitic state, the shape memory material power spring 108 is overpowered by the stainless steel return spring 107 thus allowing the ratchet body 106 to translate away from the leading tip 102 of the first nail section 101. Thus, a reciprocating action may be imparted to the ratchet body.

The reciprocating motion of the ratchet mechanism serves to lengthen the nail through the extension and retraction of the fingers 112. The nail is prevented from retracting by the buttress arms 113 which are rigidly held in place. The buttress arms allow the nail to extend under the influence of the reciprocating fingers 112 by a camming action imparted by the cooperative sloping faces of the buttress arms and the grooves 103. The faces of the arms and grooves opposite to the sloping faces are flattened and prevent movement in the reverse direction.

Because the ratcheting mechanism reciprocates rather than continually advances in one direction along its length, the shaft which extends from the fingers to the springs can be much shorter, allowing for a more compact bone lengthening nail. The relative positions of the fingers and the buttress arms may be reversed or, preferably, the fingers and arms can be located in the same axial plane.

Figure 7:
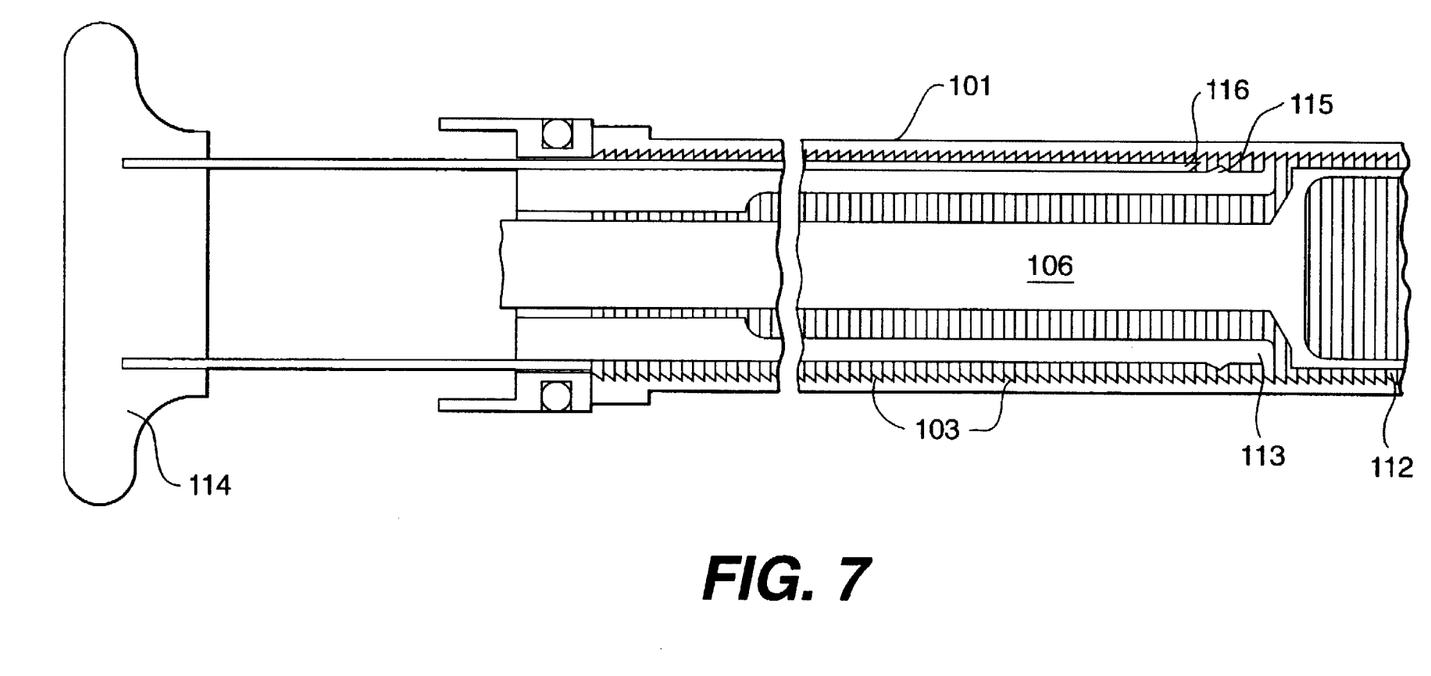
FIG. 7 illustrates the use of an insertion tool for assembling the shape memory material-powered ratchet assembly nail.

When assembling the ratchet-driven nail, a special insertion tool 114, in FIG. 7, may be used to cantilever the buttress arms away from the grooves allowing for the radial retraction of the arms. In a preferred embodiment shown in FIG. 7, the buttress arms have a camming surface 115 which cooperates with the leading edge 116 of the insertion tool 114.

Figure 8:
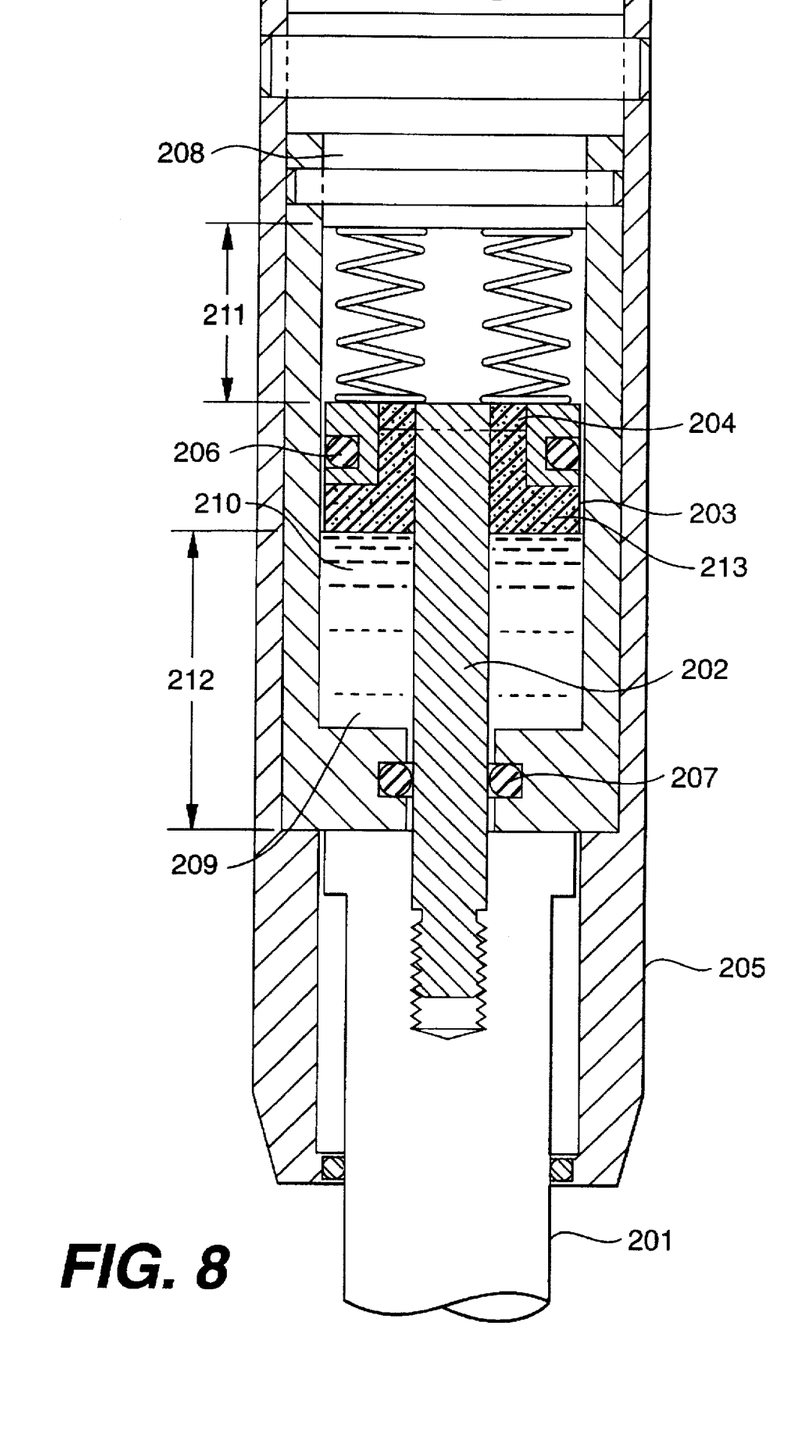
FIG. 8 illustrates an embodiment of the invention utilizing a permeable piston head powered by springs.

According to another embodiment, a spring-powered bone lengthening apparatus is an assembly of a number of interacting sections. There is a first nail section outer body 201 whose leading tip is rounded to provide ease of insertion into a cavity cut into the bone marrow of the limb to be lengthened. The first nail section outer body 201 has a certain outside diameter dimension from the leading tip longitudinally along the section to the beginning of a second cross-section which has a decreased diameter rod section 202. This section progresses for a given length to a piston head 203 whose cross-section which is larger in diameter than the rod section 202. The piston head 203 may be in the form of a bored-out cylinder where the bore 204 of the piston head 203 cylinder is designed to be shrink-fit on the outside diameter of the rod section 202. The piston head 203 is also suitably pinned to the rod section 202 so that it cannot be sheared off under the bone tensioning stress levels.

The first nail section outer body 201 inserts rod section 202 first into the first cylinder bore of a second nail section outer body 205 whose internal dimensions are larger than that of the first nail section external cross-section. The piston head 203 section of the first nail section outer body 201 slidably translates in the cylinder bore of the second nail section outer body 205 and with a suitable seal ring 206 on the piston head 203, a second rod seal ring 207, and with a suitable plug 208 creates a sealed chamber 209. This chamber is filled with an incompressible fluid 210.

According to the embodiment shown in FIG. 8, a cartridge of springs 211 is configured so that it has the force necessary to cause the bone knitting joint to stretch when the apparatus is released from its compressed configuration. Prior to placement in a medullar cavity, the apparatus may be held in the compressed configuration by a strap or any other means. When the nail is to be installed in a limb, the strap may be removed, initiating the nail lengthening process. This lengthening, however, occurs slowly enough so that the nail may be inserted into the bone cavity before it extends a significant amount.

The springs 211 may be made of nitinol or another shape memory material whose transition is calibrated to occur at or slightly below the normal body temperature of the person whose bone is being lengthened. This apparatus is stored at a temperature below the trigger temperature so that no forces are acting on the nail to cause lengthening of the apparatus.

Upon installation in the bone marrow cavity of the user, the apparatus rises to the to the temperature of the user's body which activates the shape memory material spring cartridge thereby exerting a longitudinal force between the first nail section and the second nail section and subsequently to the sections of the bone that is being lengthened. This force varies from the maximum to the minimum during the extension of the apparatus to the maximum length of travel 212 of the spring cartridge with the minimum force still exceeding that force required for the stretching of the knitting joint.

This force and travel would occur at an uncontrolled rate except for the fact that the piston head integral with the first nail section must move through the incompressible fluid which fills the cylinder in the second nail section. This motion through the fluid is accomplished by the passage of the fluid through a permeable material 213 of which the piston head 203 is fabricated. This material is designed to allow the pressurized fluid, pressurized by the spring cartridge force to permeate at the desired rate of longitudinal stretching prescribed by the surgeon in charge of the bone lengthening operation. Thus, the migration of the piston head through the fluid operates as a velocity limiter for the traveling piston head and lower section of the nail with respect to the upper section of the nail. This embodiment provides a totally automated bone lengthening procedure which progresses at a controlled rate from start of the process to the completion of the process.

Figure 9:
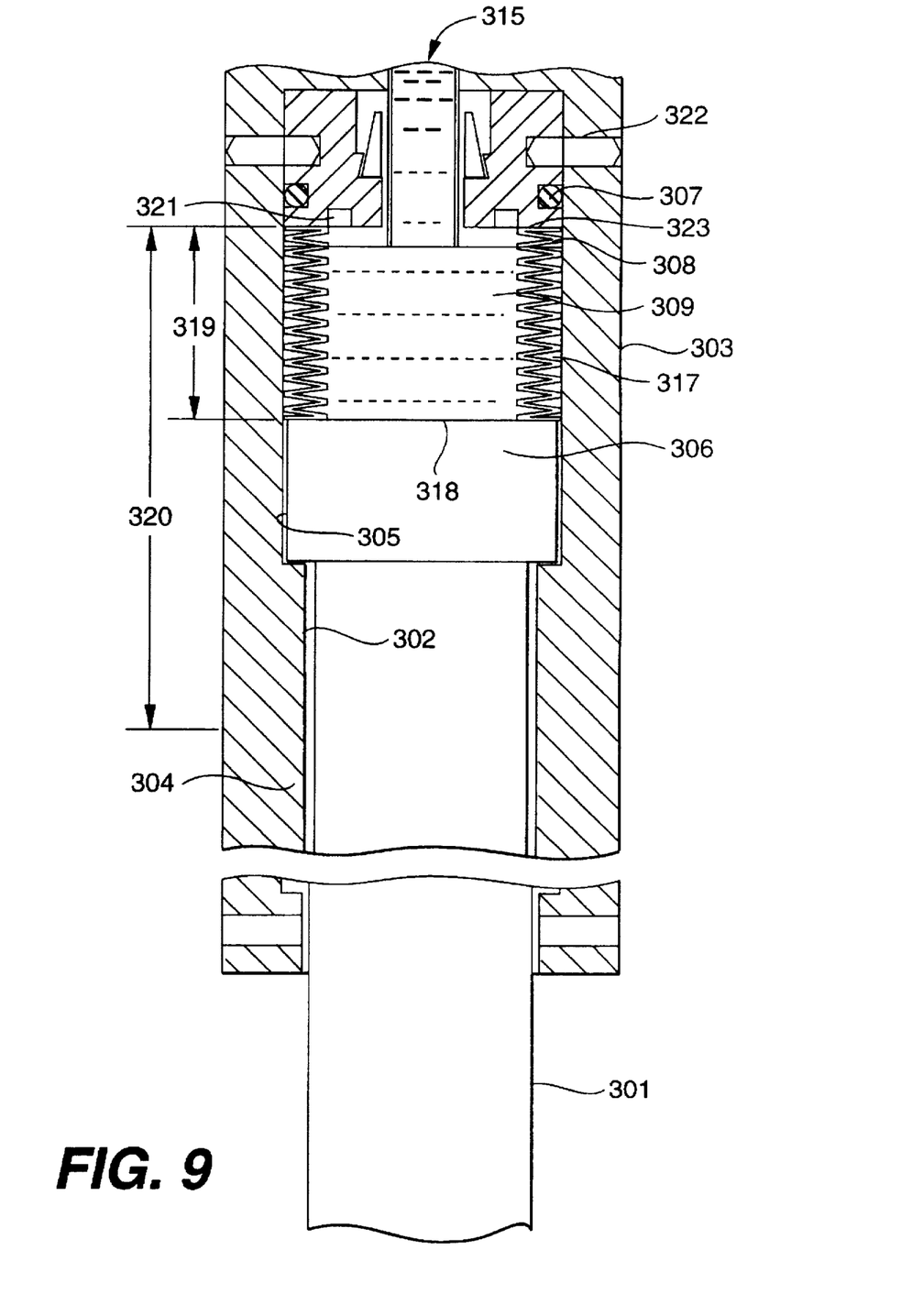
FIG. 9 illustrates an embodiment of the invention utilizing a bellows.

According to yet another embodiment shown in FIG. 9, a first nail section outer body 301 having a rounded nose section fits into the cylinder bore 302 of a second nail section outer body 303 whose internal dimensions are larger than that of the first nail section external cross-section. The bore 302 may have internal splines 304 which mate with external spline sections 305 of the first nail. The splines 304 and 305 may extend along the entire length of both the cylinder bore and first nail section body or only over certain longitudinal sections of each. The interaction between these mating spline sections restricts the torsional motion of the first nail section body 301 with respect to the second nail section. A piston head 306 section of the first nail section body 301 slidably translates in the cylinder bore 302 of the second nail section outer body 303 and with a suitable seal ring on the piston head and with a suitable plug 307 held in place by pin 322 creates a sealed chamber 308. This chamber is filled with an incompressible fluid 309 communicatively connected to a source of fluid from, preferably, a pump. The splines may be used in any of the embodiments previously described.

Figure 10:
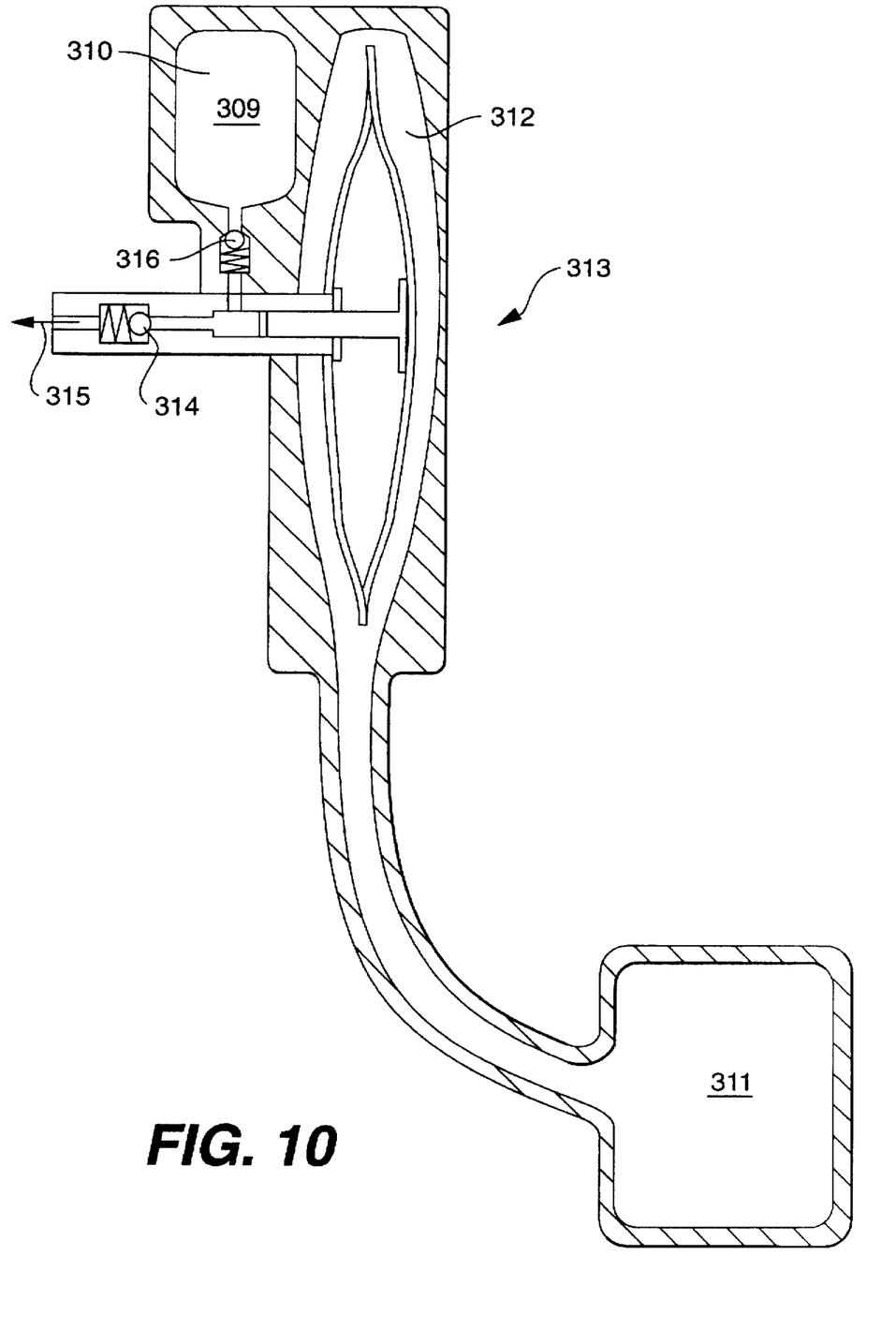
FIG. 10 illustrates an implantable pump which may be used in combination with the bellows pump embodiment of the invention.

A pump which may be used in this embodiment is shown in FIG. 10, and is communicatively connected to a reservoir 310 of fluid 309 of sufficient capacity to fill the entire cylinder chamber 308 when the first nail section outer body 301 has been longitudinally translated to its maximum extension with respect to the second nail section outer body 303. The pump is designed to be totally implanted under the epidermis along with the mated nail sections 301 and 303. It may be battery-powered by an implanted rechargeable source or designed to be activated by an externally coupled source such as an electromagnetically-operated coil or equivalent mechanism.

In operation, a source of fluid 311 is pressurized thereby compressing a bladder area 312 surrounding the fluid injection rod 313. This pressure forces the rod 313 forward, thereby forcing hydraulic fluid past the check valve 314 and out of the pump 315 and into the nail. When the pressure on the bladder of fluid is released, the rod retracts creating a low-pressure region in front of the rod. This releases a check valve 316 allowing the region in front of the rod to be filled with fluid from the reservoir 310. The pump is now ready for another injection cycle.

In a related embodiment of the implantable bone lengthening apparatus, FIG. 9, the first nail section outer body 301, would be the same as just described except that the longitudinal length would be stopped at a flat end section at the end of the external splines 305. The diameter of this section is the same as that of the external splines except that the external splines are no longer required since any torsion between the first nail section body 301 and the second nail section outer body 303 is resisted by the torsional modulus of a longitudinal bellows 317 which is affixed to a flat end section 318 on one end and to the plug 307 of the second nail section outer body 303 on the other end. This longitudinal bellows 317 has a collapsed length, L1 319, which, when subtracted from its fully extended length, L2 320, would be equivalent to the desired full travel of the first nail section outer body 301 with respect to the second nail section outer body 303. The inlet end of the longitudinal bellows 317 torsionally locks into and reacts against lugs 321 against the shoulder 323 of the bore 308 in the second nail section outer body 303. Pressurized fluid 309 from the pump is injected into the middle of the flat end of the bellows at the shoulder 323 of the bore 308 of the second nail section outer body 303. The injection of pressurized fluid 309 causes the collapsed bellows to expand thereby causing the first nail section outer body 301 to translate with respect to the second nail section outer body 303. The outer contour of the fully extended longitudinal bellows and the internal contour of the bore are matching tapers so that the longitudinal bellows 317 receives lateral support along the entire length as it expands from its collapsed state to its fully extended state.

It will be apparent to those skilled in the art that various modifications and variations can be made in the disclosed process and product without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bone lengthening nail assembly comprising:
   a first nail body section;
   a second nail body section; and
   a power cartridge located within either of said first or second nail body sections and including a powered hydraulic pump which forces hydraulic fluid from a hydraulic fluid reservoir and into a sealed chamber between said first and second sections thereby forcing said first nail section to extend longitudinally relative to said second nail section, and increasing the length of said bone lengthening nail.

2. The bone lengthening nail assembly of claim 1, wherein:
   said hydraulic pump includes;
   a low pressure inlet section;
   a high pressure discharge section;
   a check valve located between said low pressure inlet section and said high pressure discharge section to prevent fluid backflow;
   a pump piston body for conveying fluid from said low pressure section through said check valve to said high pressure discharge section said pump piston body being adjacent to a first spring made of a shape memory material located on one side of the pump piston body; and
   a second spring located on the opposing side of the pump piston body, wherein the shape memory material has a first phase in which the first spring has a lower elastic modulus than said second spring and a second phase in which said first spring has a higher elastic modulus than said second spring.

3. The bone lengthening nail of claim 1, wherein:
   said first nail body section is slidably received in said second nail body section.

4. The bone lengthening nail of claim 2, wherein:
   said pump piston body has a channel longitudinally extending therethrough, said check valve being located therein to enable fluid to be passed through said pump piston body during a return stroke, but prevent fluid from passing through said pump piston body during a pressurizing stroke.

5. The bone lengthening nail of claim 2, wherein:
   a channel body is located downstream from said pump piston body, said channel body having a channel longitudinally extending therethrough and check valve located therein to enable fluid to be passed through said channel body during the pressurizing stroke, but to prevent fluid from passing through said channel body in the direction opposite to the direction in which the pump piston body is located.

6. The bone lengthening nail of claim 2, wherein said shape memory material is transformed from the first phase to the second phase by the application of heat.

7. The bone lengthening nail of claim 6, wherein said shape memory material is nitinol.

8. A hydraulic pump comprising:
   a low pressure inlet section;
   a high pressure discharge section;
   a check valve located between said low pressure inlet section and said high pressure discharge section to prevent fluid backflow;
   a pump piston body for conveying fluid from said low pressure section through said check valve to said high pressure discharge section said pump piston body being adjacent to a first spring made of a shape memory material located on one side of the pump piston body; and
   a second spring located on the opposing side of the pump piston body, wherein the shape memory material has a first phase in which the first spring has a lower elastic modulus than the second spring, and a second phase in which said first spring has a higher elastic modulus than said second spring.

9. The hydraulic pump of claim 8, wherein:
   said pump piston body has a channel longitudinally extending therethrough said check valve being located therein to enable fluid to be passed through said pump piston body during a return stroke, but prevent fluid from passing through said pump piston body during a pressurizing stroke.

10. The hydraulic pump of claim 8, wherein:
    a channel body is located downstream from said pump piston body, said channel body having a channel longitudinally extending therethrough and cheek valve located therein to enable fluid to be passed through said channel body during a pressurizing stroke, but to prevent fluid from passing through said channel body in the direction opposite to the direction in which the pump piston body is located.

11. The hydraulic pump of claim 8, wherein said shape memory material is transformed from the first phase to the second phase by the application of heat.

12. The hydraulic pump of claim 11, wherein said shape memory material is nitinol.

13. A bone lengthening nail assembly comprising:
    a first nail body section having grooves located therein and a longitudinal axis;
    a second nail body section;
    a reciprocating ratchet mechanism located in said second nail body section and extending into said first nail body section;

fingers located on said ratchet mechanism which extend into said grooves; and a shape memory material spring attached to said ratchet mechanism which has a first phase in which said spring is compact and a second phase in which said spring is extended said shade memory material causing said ratchet mechanism to alternately move back and forth along the longitudinal axis of the first nail body section in a reciprocating movement.

14. The bone lengthening nail of claim 13, wherein:

said grooves have a first sloping face located in the direction of said second nail body section and a second face in the direction of said first body section; and said fingers have faces which cooperate with said groove faces such that said fingers can translate relative to said grooves only in the direction away from said first nail body section.

15. The bone lengthening nail of claim 13, wherein:

second springs oppose said shape memory material springs and have an elastic modulus value between the elastic modulus of the first phase and the elastic modulus of the second phase.

16. The bone lengthening nail of claim 15, wherein said shape memory material springs and said second springs are belleville springs.

17. The bone lengthening nail of claim 13, wherein said shape memory material is nitinol.

18. The bone lengthening nail of claim 13, wherein:

said grooves have a first sloping face located in the direction of said second nail body section and a second face in the direction of said first body section; and buttress arms are rigidly attached to said second nail body section, extend into said first nail body section, and have faces which cooperate with said groove faces such that said first body section can translate relative to said buttress arms only in the direction away from said second nail body section.

19. The bone lengthening nail of claim 18, wherein:

said fingers and said buttress arms are located in the same plane perpendicular to the longitudinal axis of said first nail body section.

20. A bone lengthening nail assembly comprising:

a first nail body section and a second nail body section;

a chamber located in said second nail body section, said chamber filled with fluid;

a permeable piston head attached to said first nail body section and extending into said chamber; and springs which force said permeable piston head to move longitudinally through said chamber, thereby forcing said fluid to permeate through said piston head.

21. The bone lengthening nail of claim 20, wherein said springs are made of a shape memory material.

22. The bone lengthening nail of claim 21, wherein said shape memory material is nitinol.

23. A bone lengthening nail assembly comprising:

a first nail body section and a second nail body section;

a chamber located in said second nail body section;

a piston head attached to said first nail body section and extending into said chamber;

a longitudinally expanding bellows located in said chamber and attached to said piston head and second nail body section, wherein said bellows comprises a sealed volume which expands as said bellows is filled with fluid; and a pump for falling said bellows with a fluid, thereby causing said bellows to expand, and causing said nail to extend.

24. The bone lengthening nail of claim 23, wherein said pump includes a fluid injection rod surrounded by a pressurizable bladder attached to a pressure source, said fluid injection rod being actuable, by said bladder to inject the fluid into the bellows.

* * * * *

UNITED STATES PATENT AND TRADEMARK OFFICE
CERTIFICATE OF CORRECTION

PATENT NO. : 5,626,581
DATED : May 6, 1997
INVENTOR(S) : John H. Staehlin et al.

It is certified that error appears in the above-identified patent and that said Letters Patent is hereby corrected as shown below:

Claim 9, Col. 10, line 42, "therethrough said" should read --therethrough, said--.

Claim 10, Col. 10, line 50, "cheek" should read --check--.

Claim 13, Col. 11, line 6, "extended siad shade" should read --extended, said shape--.

Signed and Sealed this

Ninth Day of September, 1997

BRUCE LEHMAN

*Attest:*

*Attesting Officer*     Commissioner of Patents and Trademarks